(12) United States Patent
Klemer et al.

(10) Patent No.: US 9,096,892 B1
(45) Date of Patent: Aug. 4, 2015

(54) NUCLEIC ACID AMPLIFICATION AND MONITORING APPARATUS

(75) Inventors: David P. Klemer, Whitefish Bay, WI (US); Daniel R. Klemer, Lexington, KY (US); Donald S. Chen, New York, NY (US); Jennifer S. Ito, New York, NY (US)

(73) Assignee: K2 Biomicrosystems, LLC, Geneva, IL (US)

( * ) Notice: Subject to any disclaimer, the term of this patent is extended or adjusted under 35 U.S.C. 154(b) by 198 days.

(21) Appl. No.: 13/021,506

(22) Filed: Feb. 4, 2011

(51) Int. Cl.
| | |
|---|---|
| *C12Q 1/68* | (2006.01) |
| *C12P 19/34* | (2006.01) |
| *C12M 1/34* | (2006.01) |
| *G01N 33/543* | (2006.01) |

(52) U.S. Cl.
CPC ........ *C12Q 1/6827* (2013.01); *G01N 33/54366* (2013.01)

(58) Field of Classification Search
None
See application file for complete search history.

(56) References Cited

U.S. PATENT DOCUMENTS

| | | | |
|---|---|---|---|
| 6,144,448 A * | 11/2000 | Mitoma | ........................ 356/317 |
| 6,174,670 B1 | 1/2001 | Wittwer et al. | |
| 6,369,893 B1 | 4/2002 | Christel et al. | |
| 6,699,713 B2 | 3/2004 | Benett et al. | |
| 6,825,927 B2 | 11/2004 | Goldman et al. | |
| 7,102,131 B2 | 9/2006 | Spolaczyk et al. | |
| 7,122,799 B2 | 10/2006 | Hsieh et al. | |
| 7,173,702 B2 | 2/2007 | Mauer et al. | |
| 7,315,376 B2 | 1/2008 | Bickmore, Jr. et al. | |
| 7,498,164 B2 * | 3/2009 | Oldham et al. | ............ 435/288.7 |
| 7,521,179 B2 | 4/2009 | Bachi | |
| 7,636,160 B2 | 12/2009 | Oldham et al. | |
| 7,749,736 B2 | 7/2010 | Kordunsky et al. | |
| 7,767,439 B2 | 8/2010 | Oh et al. | |
| 7,799,557 B2 | 9/2010 | Oh et al. | |
| 2004/0072278 A1 * | 4/2004 | Chou et al. | ...................... 435/29 |
| 2006/0223169 A1 | 10/2006 | Bedingham et al. | |
| 2007/0211985 A1 | 9/2007 | Duer | |
| 2007/0281322 A1 | 12/2007 | Jaffe et al. | |
| 2008/0030628 A1 | 2/2008 | Lundquist et al. | |
| 2008/0125330 A1 * | 5/2008 | Cady et al. | ...................... 506/17 |
| 2010/0137152 A1 | 6/2010 | Gorfinkel et al. | |

OTHER PUBLICATIONS

Richards et al., "Optically Modulated Fluorophores for Selective Fluorescence Signal Recovery," J. Am. Chem. Soc., Apr. 2009, vol. 131, No. 13, pp. 4619-4621.*

* cited by examiner

*Primary Examiner* — Young J Kim
(74) *Attorney, Agent, or Firm* — Boyle Fredrickson, S.C.

(57) ABSTRACT

The present invention relates generally to monitoring of biochemical amplification reactions using electromagnetic radiation, and more particularly to an apparatus for optical monitoring of isothermal and thermally-cycled amplification reactions using radiation ranging from the ultraviolet region through the infrared regions of the electromagnetic spectrum. Moreover, the method discussed herein could be similarly applied to any process that results in biochemical amplification, regardless of the specific technique employed.

17 Claims, 6 Drawing Sheets

NUCLEIC ACID AMPLIFICATION AND MONITORING APPARATUS

FIELD OF INVENTION

The present invention relates to the field of biomolecule amplification reactions, and more particularly to an apparatus for optical monitoring of biomolecule amplification reactions using electromagnetic radiation.

GLOSSARY

Figure 1:
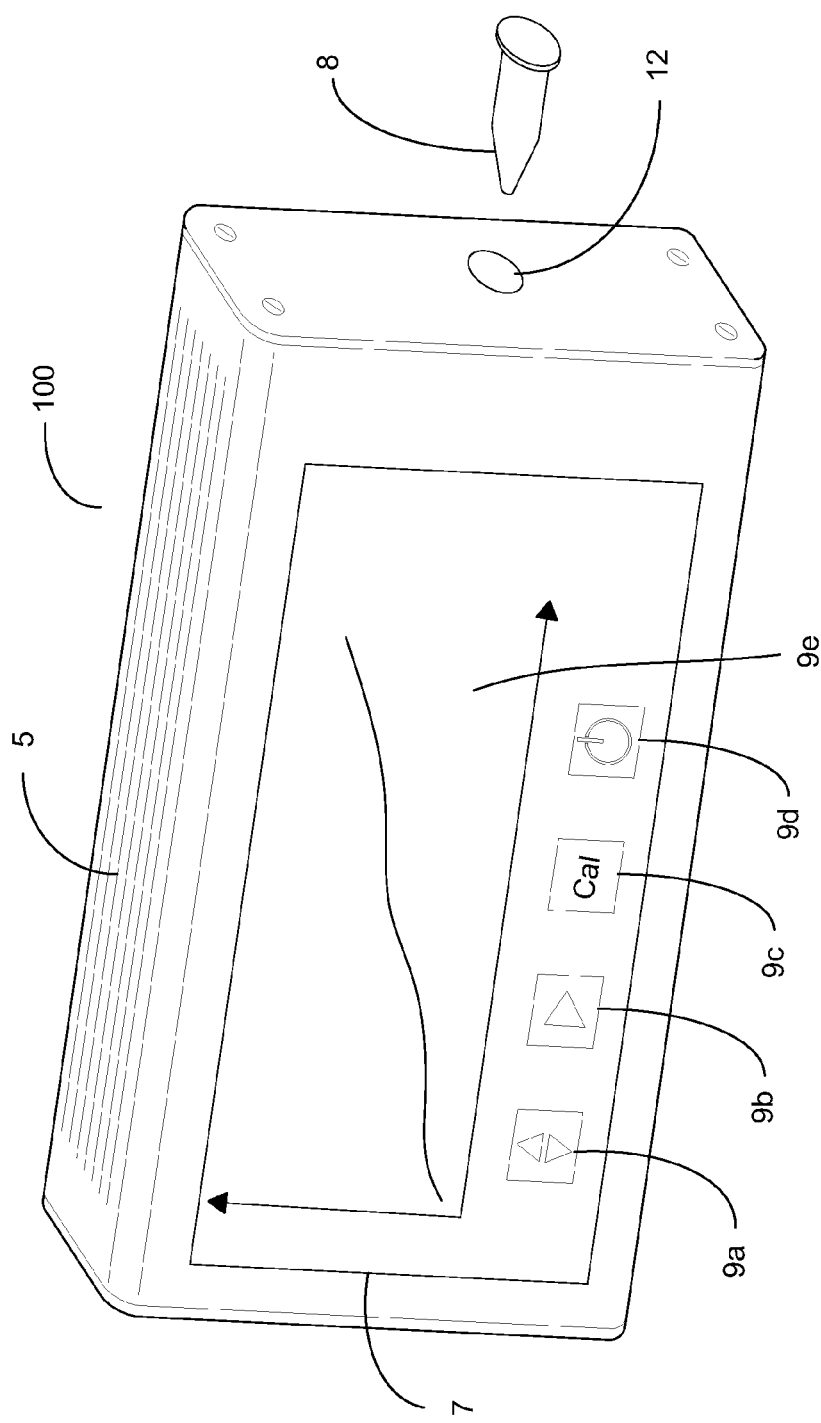
FIG. 1 illustrates a perspective view of an exemplary embodiment of nucleic acid amplification and monitoring apparatus with visual output capability.

As used herein, the term "nucleic acid" refers to a biological polymer of nucleotide bases, and may include but is not limited to deoxyribonucleic acid (DNA), ribonucleic acid (RNA), micro RNA (miRNA), and peptide nucleic acid (PNA).

As used herein, the term "nucleic acid amplification" refers to a process by which a limited quantity of nucleic acid undergoes a biochemical reaction in which a larger quantity of nucleic acid is generated.

As used herein, the term "tissue sample" refers to a quantity of cellular or sub-cellular material extracted from a prokaryotic or eukaryotic organism, or other cellular or sub-cellular material, which potentially contains nucleic acid.

As used herein, the term "tissue sample chamber" refers to a receptacle structurally capable of holding or containing a tissue sample tube or other removable component which contains a tissue sample and facilitates insertion and removal of a tissue sample from a tissue sample chamber.

As used herein, the term "output" refers to any discernible audio or visual signal known in the art. For example, a visual output may be a computer interface, touch screen, liquid crystal display (LCD) screen, personal communication device display, or any other visual component on which data or output may be displayed and viewed by a user. An output may be integrally constructed with other components of nucleic acid amplification monitoring apparatus into a single device, or may be located on another device to which a signal is sent from the nucleic acid amplification and monitoring apparatus.

As used herein, the term "quantitative result" refers to a numerical value which is related to the concentration of nucleic acid being measured.

As used herein, the term "qualitative result" refers to a binary result which indicates presence or absence of a specified nucleic acid sequence.

As used herein, the term "photon" refers to a unit particle of electromagnetic energy.

As used herein, the term "conduit" refers to a passageway of any shape, which serves to direct the path of photons, and which may contain one or more optical components.

As used herein, the term "modulator" refers to a component which may cause the amplitude, intensity, frequency, or other property of a signal to vary.

As used herein, the term "demodulator" refers to a device which extracts an information-bearing signal from a modulated signal.

As used herein, the term "signal processor" refers to a device which performs mathematical operations on a signal. A demodulator is one example of a signal processor.

As used herein, the term "excitation beam" refers to energy which is used to stimulate a sample.

As used herein, the term "emission beam" refers to energy which is produced by a sample when appropriately excited.

BACKGROUND

Biomolecules, such as deoxyribonucleic acid (DNA) and other nucleic acids, play an important role in cellular functioning as well as control of processes at the tissue, organ, system, and organism level. DNA is a biomolecule formed from two helically-arranged strands; each strand is a biopolymer formed from a linear sequence of four fundamental nucleotide units or bases—adenine, cytosine, guanine and thymine, abbreviated respectively as A, C, G and T. Each base on one strand is hydrogen bonded to exactly one complementary base (A with T and G with C) on the opposite strand, thereby forming a nucleotide base pair. DNA found in a human cell typically consists of approximately three billion base pairs. The specific sequence of A, C, G and T bases which forms the DNA molecule within the cells of an individual is referred to as that individual's genotype, which can vary from person to person. Subsections of the DNA biomolecule may serve to encode for specific proteins; these subsections may consist of several thousands (to millions) of base pairs, and are referred to as genes.

In some cases, a complete determination of the sequence of bases in a DNA molecule—referred to as "DNA sequencing"—defines an individual's genotype, and can be helpful in assessing the propensity for acquiring disease or metabolizing medications, for example. More often, however, knowledge of the sequence within a small subset of the DNA molecule is very useful. For example, confirmation of a specific sequence for a specific gene may be sufficient to assess a predisposition for the development of a certain cancer. The determination of the presence of specific subsection sequences of DNA is referred to as molecular diagnostics; in vitro molecular diagnostics is the term applied when this determination is accomplished using a sample of tissue extracted from an organism.

Molecular diagnostic techniques are typically based on the use of primer molecules, which are short, specific sections of single-stranded DNA used to identify the presence of specific genes or specific sequences within DNA molecules. Primer molecules may, for example, be gene-specific, disease-specific, or organism-specific. Primers and associated reagents are typically mixed with sample of unknown DNA in solution, and the presence of a specific type of DNA is determined through an amplification reaction: if a given DNA sequence is present in the unknown sample, it can be amplified and detected as the reaction proceeds. A widely-used form of amplification is based on the polymerase chain reaction (PCR) technique.

Detection of amplification products (referred to as amplicons) or monitoring of the amplification process itself may be accomplished in numerous ways. One of the most common techniques detects a fluorescence optical signal which increases in intensity during the amplification process if the target DNA sequence is present in an unknown sample. Traditional detection approaches for monitoring the progress of an amplification process use optical sensors (e.g., photodiodes or phototransistors) for sensing the fluorescent light.

The ability of a monitoring system to detect the fluorescence signal ultimately impacts the sensitivity with which low concentrations of DNA can be detected. In many cases the initial quantity of DNA may be extremely small. One problem known in the prior art is the inability to detect very small quantities of DNA due to susceptibility to noise sources inherent in any monitoring system, including optical noise, detector noise, and electrical signal processing noise.

It is desirable to have an apparatus capable of both amplifying nucleic acid under optimal conditions and monitoring the amplification while rejecting undesired signals introduced by sources of noise.

It is desirable to have an apparatus capable of amplifying and monitoring nucleic acid with improved sensitivity for nucleic acid detection.

SUMMARY OF THE INVENTION

The present invention is an apparatus for amplifying and monitoring the amplification of nucleic acid. A tissue sample is placed into a tissue sample chamber and an excitation beam from a light excitation component is directed onto the tissue sample. One or more properties of the excitation beam are modulated using a modulator. Electromagnetic energy emitted from the tissue sample is collected and directed onto a photodetector, which produces an electrical signal in response to the collected light. The electrical signal is then demodulated by a signal processor. The nucleic acid amplification and monitoring apparatus also includes a power source, and an output which allows the amplification of the nucleic acid in the tissue sample to be monitored.

DETAILED DESCRIPTION OF INVENTION

For the purpose of promoting an understanding of the present invention, references are made in the text to exemplary embodiments of an apparatus for amplifying and monitoring the amplification of nucleic acid, only some of which are described herein. It should be understood that no limitations on the scope of the invention are intended by describing these exemplary embodiments. One of ordinary skill in the art will readily appreciate that alternate but functionally equivalent components, materials, and layouts may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related.

FIG. 1 shows a perspective view of an exemplary embodiment of nucleic acid amplification and monitoring apparatus 100. In the embodiment shown, nucleic acid amplification and monitoring apparatus 100 is comprised of outer housing 5 with tissue sample port 12 through which tissue sample chamber 10 (FIG. 5) is accessed, and visual display 7. Outer housing 5 encases tissue sample chamber 10 and other components including, but not limited to a light excitation component, an excitation collimating lens, an excitation filter, an emission filter, an emission collimating lens, a temperature sensor, temperature control circuitry, a modulator, and a signal processor.

In the embodiment shown, visual display 7 is a touch screen with display capability for viewing and controlling nucleic acid amplification and includes a plurality of controls 9a, 9b, 9c, 9d, 9e. In the embodiment shown, visual display 7 has temperature control 9a, amplification initiation control 9b, calibration control 9c, power control 9d, and display adjustment control 9e which controls options for a graphical, numeric, quantitative, or qualitative measurement representation and display of data. In the embodiment shown, 9c calibration control is used to calibrate the system using a known sample so that the system reflects accurate nucleic acid concentration and/or to gauge the accuracy and performance of the particular device.

In various embodiments, visual display 7 may include more or fewer or varying types of controls. In other embodiments, controls 9a, 9b, 9c, 9d, 9e may be physical controls, such as levers, buttons, switches, and dials; electronic signals; voice activated or timed controls; and/or a remote or local user interface. In other embodiments, visual display 7 may be eliminated and replaced with an audio output signal, such as a synthesized voice signal. In still other embodiments, visual display 7 may be eliminated and replaced with means for generating an electronic representation of the data, which may be subsequently stored or transmitted to a receiver capable of decoding said electronic representation of the data.

In the embodiment shown, visual display 7 is integrally constructed with nucleic acid amplification and monitoring apparatus 100; however, in various other embodiments visual display 7 may be a visual display on another device to which a signal is sent from nucleic acid amplification and monitoring apparatus 100.

Figure 5:
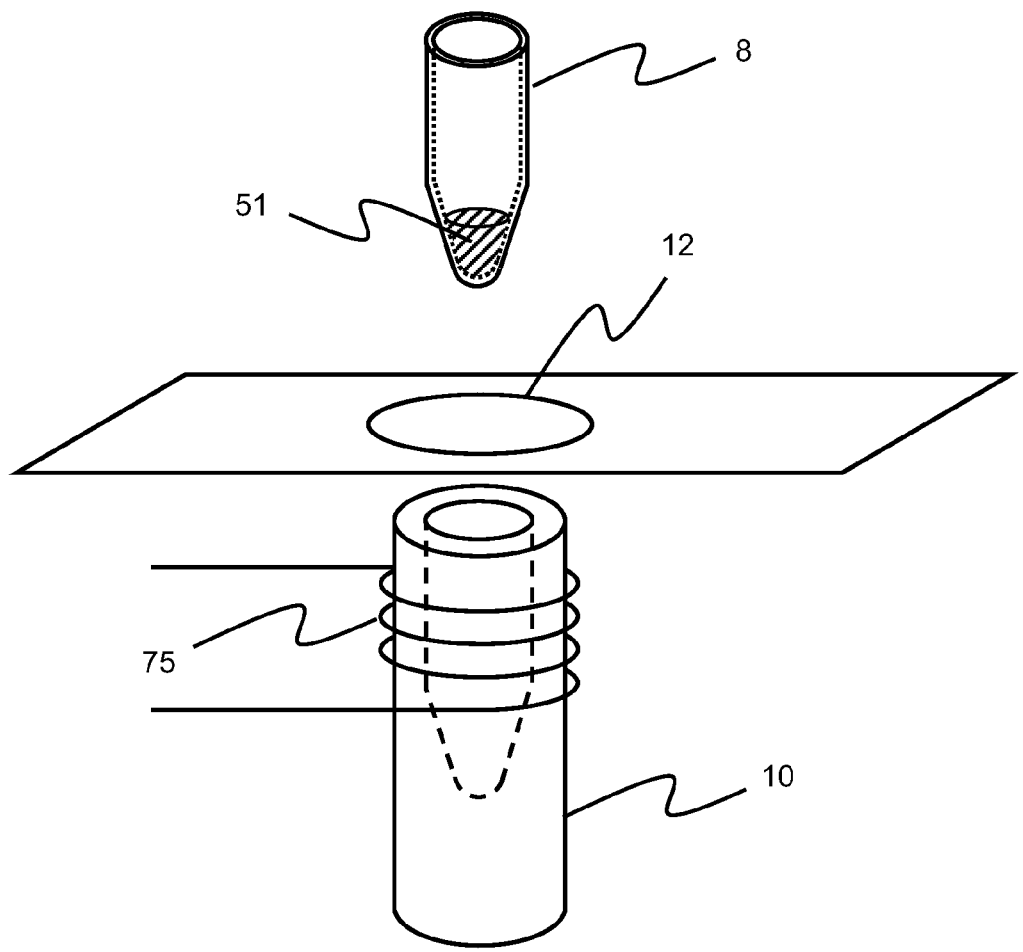
FIG. 5 illustrates an exemplary embodiment of a heated tissue sample chamber of nucleic acid amplification and monitoring apparatus.

Also visible in FIG. 1 is a tissue sample enclosed in tissue sample tube 8 (of a type known in the art for storing tissue samples). Tissue sample tube 8 is inserted through tissue sample port 12 into tissue sample chamber 10 (FIG. 5). In the embodiment shown, tissue sample tube 8 is a transparent tube which allows light to be absorbed by or emitted from a sample and subsequently detected for measurement.

In the embodiment shown, nucleic acid amplification and monitoring apparatus 100 is portable and hand-held; however, in other embodiments, nucleic acid amplification and monitoring apparatus 100 may be any size.

Figure 2:
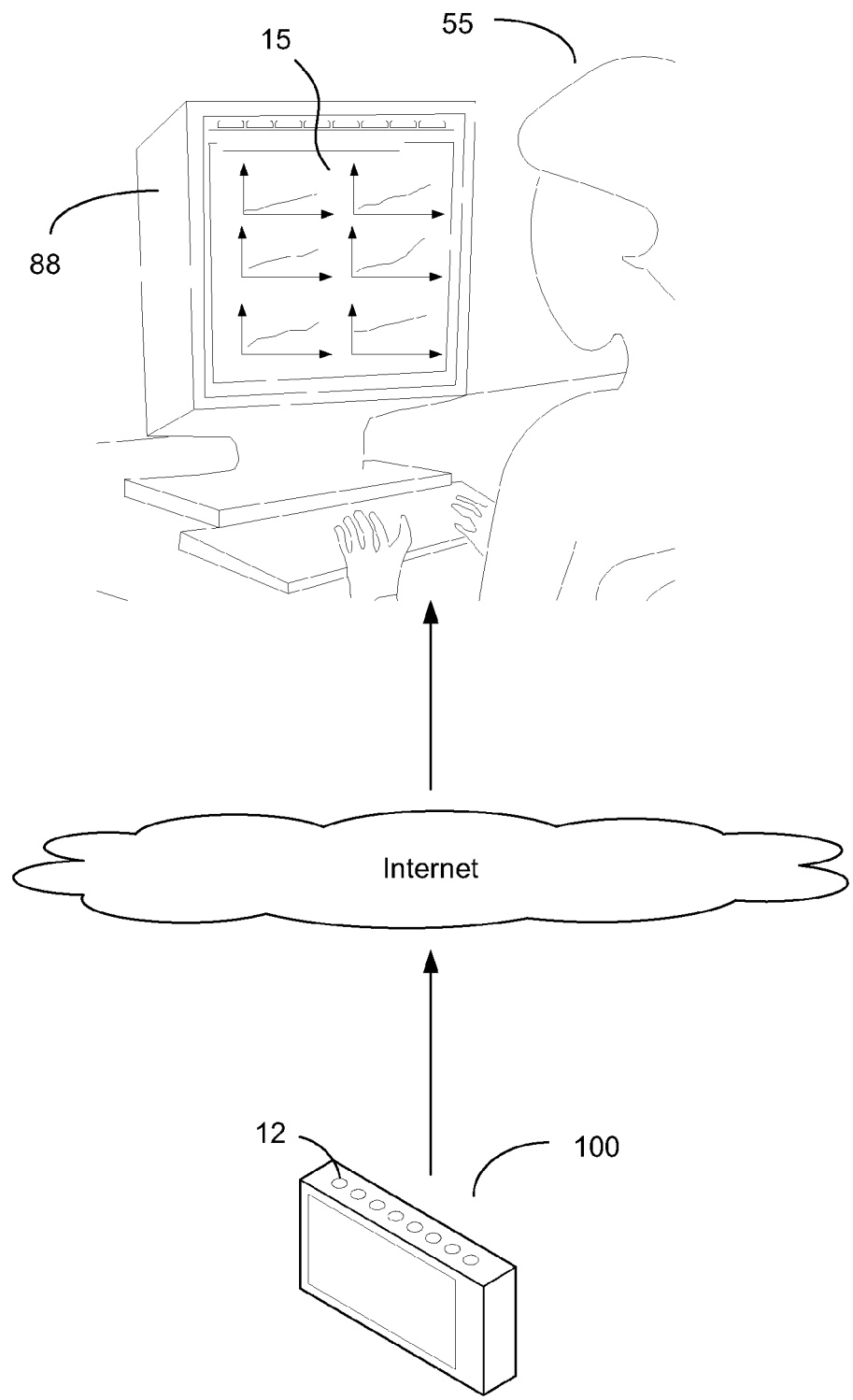
FIG. 2 illustrates a perspective view of an alternate embodiment of nucleic acid amplification and monitoring apparatus with an external visual output.

FIG. 2 illustrates an alternative embodiment of nucleic acid amplification and monitoring apparatus 100 which is integrated with external visual display 15. In the embodiment shown, nucleic acid amplification and monitoring apparatus 100 includes a plurality of tissue sample ports 12 and external visual display 15 is capable of displaying readings for multiple tissue samples.

In the embodiment shown, nucleic acid amplification and monitoring apparatus 100 includes a means for transmitting diagnostic data derived from signal processor 40 (FIG. 4) to external device 88 to be displayed on a single display device, or over a local or wide area network. In the embodiment shown, multiple samples are analyzed in a laboratory using nucleic acid amplification and monitoring apparatus 100, and diagnostic data is transmitted over the internet for review on external visual display 15 by technician 55.

Figure 3:
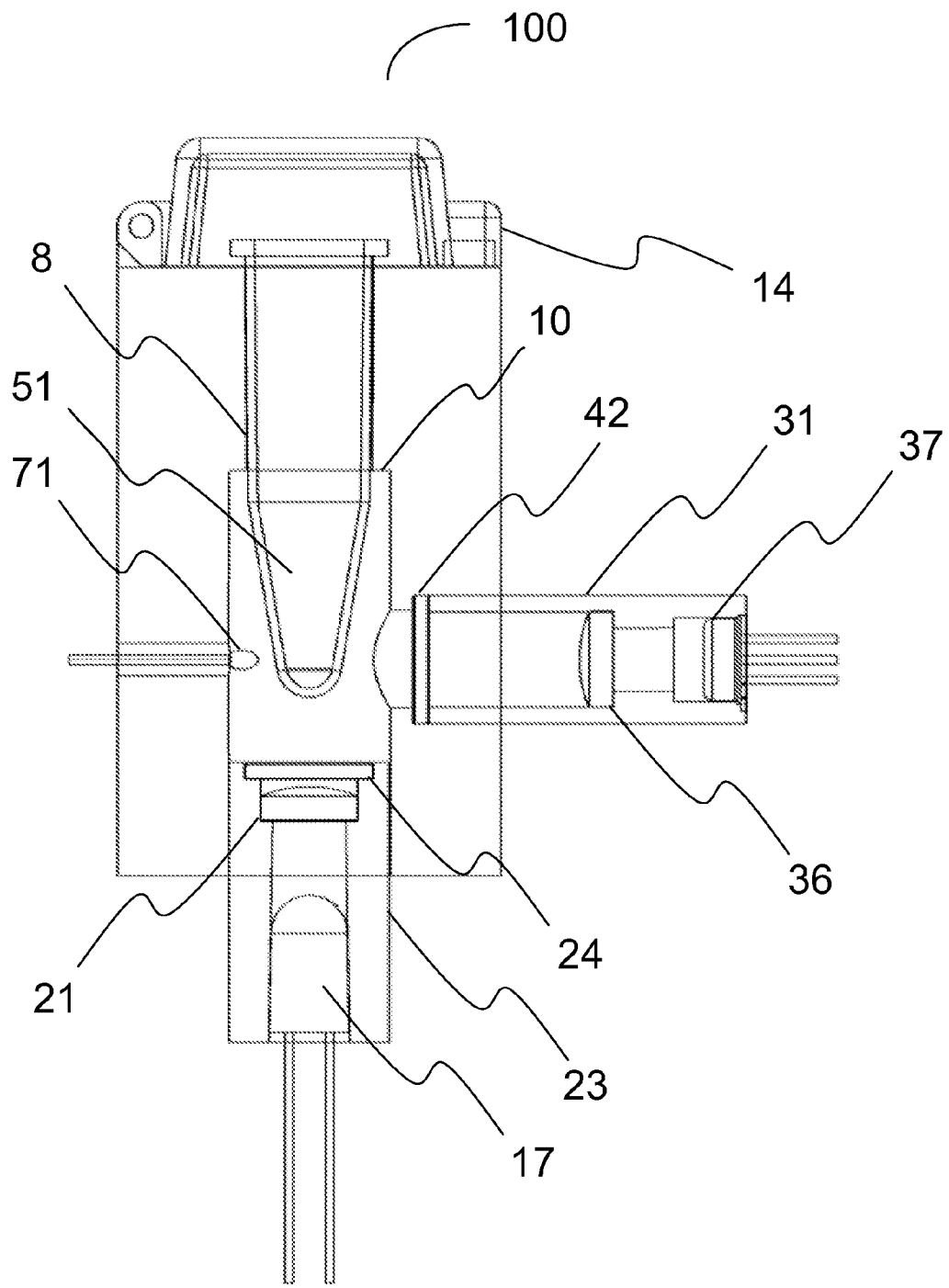
FIG. 3 illustrates an exemplary embodiment of a tissue sample tube in a tissue sample chamber of nucleic acid amplification and monitoring apparatus.

FIG. 3 illustrates an exemplary embodiment of tissue sample tube 8 in tissue sample chamber 10 of nucleic acid amplification and monitoring apparatus 100. In the embodiment shown, tissue sample chamber 10 is a receptacle structurally capable of holding tissue sample tube 8 having a measurable amount of tissue sample 51. In an exemplary embodiment, tissue sample 51 contains nucleic acid, standard reagents, and a fluorescent molecule (of a type known in the art for monitoring nucleic acid amplification processes), which produces fluorescent light when illuminated by an appropriate wavelength of excitation light.

Also visible in FIG. 3 are light excitation component 17, excitation collimating lens 21, excitation filter 24, emission filter 42, emission collimating lens 36, photodetector 37, light insulating cover 14, and temperature sensor 71.

Light excitation component 17 is a component which illuminates, excites, or initiates photonic activation of a fluorescent molecule in tissue sample 51. Light excitation component 17 produces excitation beam 26 (FIG. 4) which is directed to tissue sample tube 8 and tissue sample 51. Before excitation beam 26 reaches tissue sample 51, excitation beam 26 passes through excitation collimating lens 21 and excitation filter 24. Excitation collimating lens 21 aligns the photons in excitation beam 26 and excitation filter 24 filters excitation beam 26, limiting the bandwidth of the excitation photons reaching tissue sample 51.

Excitation beam 26 excites the fluorescent molecule in tissue sample 51, which produces a fluorescent signal proportional to the concentration of the target nucleic acid molecule, creating emission beam 45 (FIG. 4), which has a wavelength greater than that of excitation beam 26. Emission beam 45 passes through emission filter 42 and emission collimating lens 36 before reaching photodetector 37. Emission collimating lens 36 aligns the fluorescent photons in emission beam 45 and emission filter limits the bandwidth of emission beam 45.

Excitation filter 24 and emission filter 42 isolate excitation and emission light, respectively, preventing photons from excitation beam 26 from reaching photodetector 37. Excitation filter 24 and emission filter 42 have different wavelength ranges and vary depending on the light excitation component and the fluorescent molecule used.

In an exemplary embodiment, excitation filter 24, excitation collimating lens 21, and light excitation component 17 are supported within excitation conduit 23. Emission filter 42, emission collimating lens 36, and photodetector 37 are supported within emission conduit 31.

Light excitation component 17 may be any type of coherent or non-coherent light source known in the art, including but not limited to, a solid-state laser, diode laser, gas laser, dye laser, light emitting diode (LED), superluminescent diode (SLD), non-coherent lamp, or any other light source known in the art. In embodiments in which light excitation component 17 is an LED, excitation collimating lens 21 may or may not be used. Excitation collimating lens 21 and/or excitation filter 24 may also be omitted with other types of light sources, such as a solid-state laser, which emits a characteristically very narrow wavelength, eliminating the need for excitation filter 24.

In various embodiments, excitation beam 26 and emission beam 45 (FIG. 4) have a wavelength ranging from 10 nm to 10 µm.

In the embodiment shown, excitation filter 24 and emission filter 42 are filters known in the art. In various other embodiments, excitation collimating lens 21 and emission collimating lens 36 are replaced by an alternative collimating component known in the art, such as a collimating tube, collimating aperture, or aperture set.

In the embodiment shown, light insulating cover 14 insulates tissue sample tube 8 and tissue sample 51, preventing tissue sample 51 from being illuminated from light external to nucleic acid amplification and monitoring apparatus 100. Light insulating cover 14 may or may not be heated; however, heating of light insulating cover 14 may be desirable for preventing sample evaporation.

Figure 6:
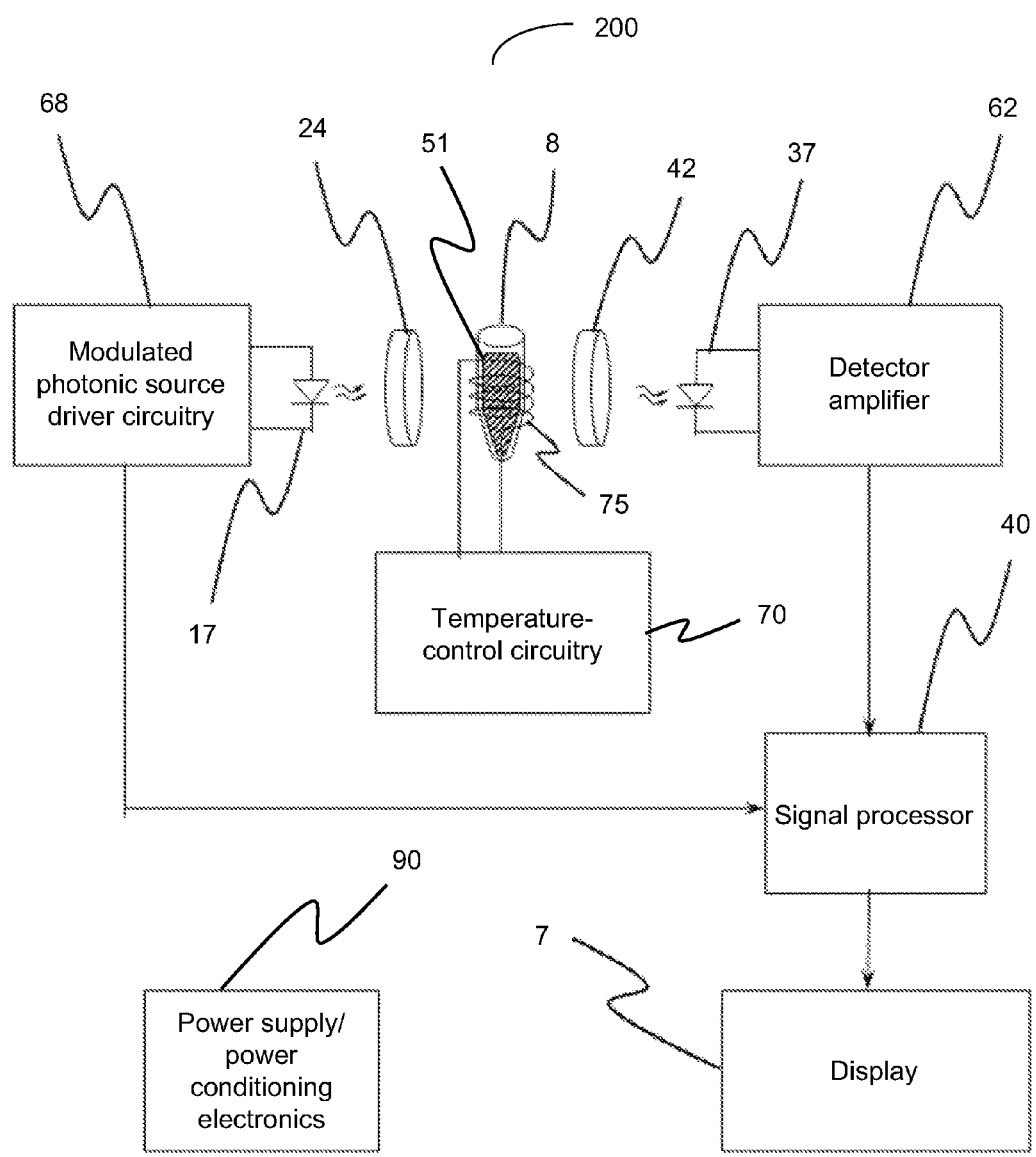
FIG. 6 illustrates a block diagram of an exemplary embodiment of nucleic acid amplification and monitoring system.

In the embodiment shown, temperature sensor 71 measures the temperature inside tissue sample chamber 10. The measured temperature is used to control the temperature of tissue sample 51 via temperature control circuitry 70 (FIG. 6).

In the embodiment shown, photodetector 37 converts photons in emission beam 45 to a measurable voltage or current signal.

Figure 4:
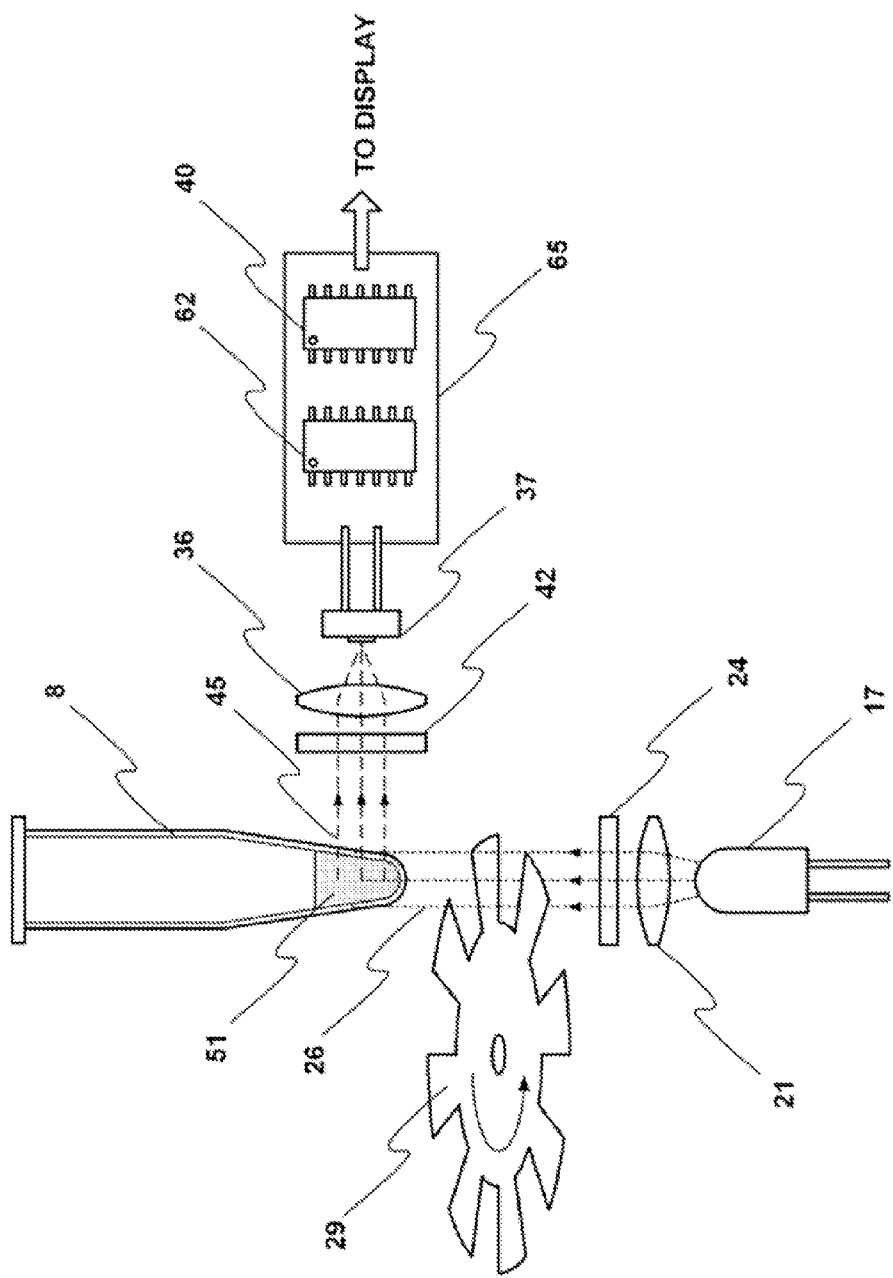
FIG. 4 illustrates an exploded view of an exemplary embodiment of a tissue sample chamber with optical assembly for nucleic acid amplification and monitoring apparatus.

FIG. 4 illustrates an exploded view of an exemplary embodiment of sample chamber with optical assembly for nucleic acid amplification and monitoring apparatus 100. Also visible in FIG. 4 are modulator 29, printed circuit board 65, amplifier 62, and signal processor 40.

In the embodiment shown, modulator 29 is a mechanical shutter (e.g., chopper wheel) that modulates excitation beam 26. In other embodiments, the mechanical shutter is omitted and replaced by an electronic circuit which modulates the light intensity produced by light excitation component 17, thereby modulating excitation beam 26. In various embodiments, modulator 29 may produce a periodic waveform or an aperiodic waveform to modulate excitation beam 26.

In the embodiment shown, emission beam 45 is converted into a voltage or current signal by photodetector 37. The signal from photodetector 37 is amplified by amplifier 62 and processed by signal processor 40.

In the embodiment shown, signal processor 40 is a device which operates on the signal from photodetector 37 to substantially separate the information-bearing component of the signal, which substantially expresses the modulation impressed by modulator 29, from the noise component, which remains substantially unmodulated at the frequency of modulator 29, thereby improving the signal-to-noise ratio of the resulting measurement. One type of signal processor, for example, forms the mathematical product of the amplified photodiode signal and a reference signal proportional to the modulation signal. Signal processor 40 may be any type of multiplier known in the art, including but not limited to, a demodulator, mixer, digital multiplier, and balanced demodulator.

Signal processor 40 produces a voltage or current which is related to the concentration of nucleic acid in tissue sample 51, and the aforementioned current or voltage is used to generate a display on visual display 7 (FIG. 1).

In various embodiments, amplifier 62 may be a logarithmic amplifier, a non-linear amplifier, a voltage amplifier, a current amplifier, a power amplifier, a transimpedance amplifier, or a transadmittance amplifier.

In various embodiments, nucleic acid amplification and monitoring apparatus 100 may further include a physical memory component for storing sample data.

FIG. 5 illustrates an exemplary embodiment of the wiring configuration for heated tissue sample chamber 10 of nucleic acid amplification and monitoring apparatus 100. In the embodiment shown, tissue sample tube 8 with tissue sample 51 is passed through tissue sample port 12 into tissue sample chamber 10, which is heated electrically by heating coil 75. Temperature control circuitry 70 (FIG. 6) controls the temperature of heating coil 75.

In various embodiments, tissue sample chamber 10 may be heated by another means, such as an electronic resistance heater, Peltier heater, chemical heater, or a photonic heater, or may be operable at room temperature or ambient temperature without the need to be heated. In still other embodiments, the temperature of tissue sample chamber 10 may be maintained at a fixed temperature, regulated, cycled, varied, controlled, and/or intermittently adjusted. For example, the temperature of tissue sample chamber 10 may be chemically controlled. In the embodiment shown, tissue sample chamber 10 is maintained at an appropriate temperature at which a nucleic amplification reaction can proceed.

In the embodiment shown, nucleic acid may be amplified using thermocycling amplification (e.g., polymerase chain reaction (PCR), quantitative PCR (Q-PCR), multiplex-PCR, asymmetric PCR). In still other embodiments, nucleic acid may be amplified using isothermal amplification using a technique known in the art (e.g., loop-mediated isothermal amplification (LAMP), helicase-dependent amplification, PAN-AC, recombinase polymerase amplification (RPA), nicking enzyme amplification reaction).

FIG. 6 illustrates a block diagram of an exemplary embodiment of nucleic acid amplification and monitoring system 200. Nucleic acid amplification and monitoring system 200 is comprised of modulated photonic source driver circuitry 68, light excitation component 17, excitation filter 24, tissue sample 51 in tissue sample tube 8, temperature-control circuitry 70, heating coil 75, emission filter 42, photodetector 37, amplifier 62, signal processor 40, visual display 7, and power supply/power conditioning electronics 90.

In the embodiment shown, modulated photonic source driver circuitry 68 modulates the intensity of excitation beam 26 (not shown) over time, temperature control circuitry 70 controls the temperature of tissue sample tube 8 and ensures that tissue sample tube 8 is heated to a temperature which allows the nucleic acid amplification reaction to proceed, and power supply/power conditioning electronics 90 provide power to nucleic acid amplification and monitoring system 200.

In the embodiment shown, light excitation component 17 emits excitation beam 26 (not shown). Excitation beam 26 is powered and modulated by photonic source driver circuitry 68, and filtered to a given wavelength range by excitation filter 24. Excitation beam 26 excites fluorescent molecules in tissue sample 51 in tissue sample tube 8 producing emission beam 45, which is proportional to the concentration of the target nucleic acid molecule in tissue sample 45. Emission beam is collected, passed through emission filter 42, and directed onto photodetector 37 and amplifier 62. Photodetector 37 converts photons in emission beam 45 to a measurable voltage or current signal and signal processor 40 multiples the temporal waveform of the detected emission beam 45 intensity by the input modulation waveform. The average value of the voltage at the output of signal processor 40 is proportional to the fluorescence intensity, and accordingly, the concentration of the target nucleic acid solution in tissue sample 51.

In various other embodiments, nucleic acid amplification and monitoring system 200 further includes excitation collimating lens 21 and emission collimating lens 36.

Nucleic acid amplification and monitoring system 200 may be used to obtain both qualitative and/or quantitative results. For example, if the fluorescence signal increases as the amplification process proceeds, then the target nucleic acid is present. The increase in fluorescence signal also causes an increase in the signals from photodetector 37 and amplifier 62, which cause an increase in the average output from signal processor 40. The increasing electrical signals are proportional to the concentration of nucleic acid being measured, allowing the concentration of the target nucleic acid to be calculated.

In various embodiments, modulated photonic source driver circuitry 68 may produce a periodic waveform or an aperiodic waveform to modulate excitation beam 26.

Nucleic acid amplification and monitoring system 200 is simultaneously highly sensitive to the fluorescence signal emitted from tissue sample 51 and insensitive to noise signals (e.g., ambient light), which interfere with measurement. The modulation and signal processor processes improve signal-to-noise ratio and increase sensitivity, allowing for measurements of small quantities of nucleic acid, which would otherwise yield a fluorescence signal obscured by noise. In addition, nucleic acid amplification and monitoring system 200 provides the optimal reaction conditions for nucleic acid amplification while simultaneously monitoring for fluorescence and rejecting optical noise signals during the reaction process.

What is claimed is:

1. A nucleic acid amplification apparatus comprising:
    a tissue sample chamber configured to receive a tissue sample therein;
    a temperature control configured to maintain the temperature of the tissue sample chamber at a substantially fixed temperature during nucleic acid amplification;
    at least one light source, the at least one light source providing a fluorescence excitation beam;
    an electronic signal modulator that produces an aperiodic waveform for imparting an aperiodic modulation on the fluorescence excitation beam to form a modulated fluorescence excitation beam configured to stimulate the tissue sample;
    at least one photodetector, the at least one photodetector detecting a fluorescence emission beam from said tissue sample and providing a corresponding output signal;
    a first conduit for directing the modulated fluorescence excitation beam onto the tissue sample chamber and the tissue sample;
    a second conduit for directing the fluorescence emission beam from said tissue sample onto said at least one photodetector;
    a logarithmic amplifier receiving the corresponding output signal from said at least one photodetector and generating a corresponding amplified signal;
    a demodulating signal processor configured to receive the amplified signal from the logarithmic amplifier and isolate therefrom a signal indicative of nucleic acid amplification in the tissue sample chamber from an electromagnetic noise signal wherein the signal indicative of nucleic acid amplification, in the tissue sample chamber substantially expresses the aperiodic modulation imparted by the modulator and the electromagnetic noise signal substantially expresses a characteristic distinguishable from the aperiodic modulation imparted by the modulator;
    a power source; and
    an output configured to communicate the signal indicative of nucleic acid amplification in the tissue sample chamber.

2. The apparatus of claim 1 wherein said temperature control is an exothermic reaction.

3. The apparatus of claim 1 wherein said apparatus further includes a means for collimating the fluorescence mission beams selected from a group consisting of a collimating tube, collimating lens, collimating aperture, and aperture set.

4. The apparatus of claim 1 which further includes an excitation filter.

5. The apparatus of claim 1 wherein said at least one light source is a coherent light source selected from a group consisting of a solid-state laser, diode laser, gas laser, and dye laser.

6. The apparatus of claim 1 wherein said at least one light source is a noncoherent light source selected from a group consisting of a light-emitting diode, superluminescent diode, and noncoherent lamp.

7. The apparatus of claim 1 which further includes a second amplifier for amplifying a signal from said at least one photodetector.

8. The apparatus of claim 7 wherein said second amplifier is an amplifier selected from a group consisting of a non-linear amplifier, voltage amplifier, current amplifier, power amplifier, transimpedance amplifier, and transadmittance amplifier.

9. The apparatus of claim 1 which further includes a housing with a port through which said tissue sample chamber is accessed.

10. The apparatus of claim 1 which further includes data transmitting capability.

11. The apparatus of claim 1 which further includes a physical memory component for storing data for at least one sample.

12. The apparatus of claim 1 wherein the temperature control further includes a heating component, said heating component is selected from a group consisting of an electronic resistance heater, Peltier heater, microwave heater, chemical heater and photonic heater.

13. The apparatus of claim 1 wherein said fluorescence excitation beam and said fluorescence emission beam have a wavelength ranging from 10 nm to 10 µm.

14. The apparatus of claim 1 wherein said modulator is an electronic control circuitry.

15. The apparatus of claim 1, wherein a means for limiting the bandwidth of the emitted fluorescence emission beam is provided.

16. An isothermal nucleic acid amplification apparatus comprising:
a tissue sample chamber configured to receive a tissue sample therein;
a heating component adjacent to the tissue sample chamber for heating the tissue sample chamber, wherein the heating component is selected from a group consisting of an electronic resistance heater, electronic joule heater, Peltier heater, chemical heater, microwave heater, and photonic heater;
a temperature sensor generating a temperature signal indicative of a temperature of the tissue sample chamber;
a temperature control receiving the temperature signal and controlling the heating component to maintain the temperature of the tissue sample chamber at a substantially fixed temperature;
a cover received at an opening to the sample chamber, wherein the cover prevents entry of ambient light into the tissue sample chamber;
at least one light source providing a fluorescence excitation beam;
an electronic signal modulator that produces an aperiodic waveform for imparting an aperiodic modulation on the fluorescence excitation beam to form a modulated fluorescence excitation beam configured to stimulate the tissue sample;
a first conduit for directing the modulated fluorescence excitation beam into the tissue sample chamber and into the enclosed tissue sample;
an optical filter located within the first conduit;
at least one photodetector configured to detect a fluorescence emission beam from the tissue sample and provide a corresponding output signal;
a second conduit for directing the fluorescence emission beam from the tissue sample onto the at least one photodetector;
an optical filter located within said second conduit;
at least one logarithmic amplifier receiving the corresponding output signal from said at least one photodetector and generating a corresponding amplified signal;
a demodulating signal processor receiving the amplified signal from the at least one logarithmic amplifier and isolating therefrom an output indicative of an isothermal nucleic acid amplification process in the tissue sample chamber from a noise signal wherein the output indicative of the isothermal nucleic acid amplification process substantially expresses the aperiodic modulation imparted by the modulator and the noise signal substantially expresses a characteristic distinguishable from the aperiodic modulation imparted by the modulator;
a power source;
a graphical display output representing said output indicative of nucleic acid amplification process in visual form; and
a physical memory component for storing data generated during said nucleic acid amplification process.

17. The apparatus of claim 16 including a transmitter for electronically transmitting the output indicative of nucleic acid amplification process to a computer.

* * * * *

UNITED STATES PATENT AND TRADEMARK OFFICE
CERTIFICATE OF CORRECTION

| | | |
|---|---|---|
| PATENT NO. | : 9,096,892 B1 | Page 1 of 1 |
| APPLICATION NO. | : 13/021506 | |
| DATED | : August 4, 2015 | |
| INVENTOR(S) | : David P. Klemer et al. | |

It is certified that error appears in the above-identified patent and that said Letters Patent is hereby corrected as shown below:

IN THE CLAIMS

CLAIM 1, column 8, line 54, after "amplification" delete ",";

CLAIM 3, column 8, line 67, delete "mission" and substitute therefor -- emission --.

Signed and Sealed this
First Day of December, 2015

Michelle K. Lee
*Director of the United States Patent and Trademark Office*